U S005192263A

United States Patent [19]
Kraus

[11] Patent Number: 5,192,263
[45] Date of Patent: Mar. 9, 1993

[54] ELECTROMEDICAL APPARATUS FOR GENERATING LOW-FREQUENCY MAGNETIC FIELDS

[76] Inventor: Werner Kraus, Augustenstrasse 41, 8000 Muenchen 2, Fed. Rep. of Germany

[21] Appl. No.: 703,802

[22] Filed: May 21, 1991

[30] Foreign Application Priority Data

May 29, 1990 [DE] Fed. Rep. of Germany ... 9006057[U]

[51] Int. Cl.$^5$ ............................................. A61N 1/00
[52] U.S. Cl. ...................................... 600/14; 128/422
[58] Field of Search ............... 600/9, 13, 14; 128/421, 128/422

[56] References Cited

U.S. PATENT DOCUMENTS 4,998,913 3/1991 Atwood, Jr. ..................... 600/14

FOREIGN PATENT DOCUMENTS 1150361 7/1983 Canada .
0132051 1/1985 European Pat. Off. .
0270828 6/1988 European Pat. Off. .
0367338 5/1990 European Pat. Off. .
8910196 1/1990 Fed. Rep. of Germany .
2528709 6/1983 France .
2057889 4/1981 United Kingdom .

Primary Examiner—Lee S. Cohen
Assistant Examiner—J. P. Lacyk
Attorney, Agent, or Firm—Iandiorio & Dingman

[57] ABSTRACT

An electromedical apparatus for generating low-frequency magnetic fields for magnetic field therapy or treatments by the Kraus & Lechner method includes an oscillator and amplifier (10, 12) for generating low-frequency electrical oscillations of adjustable frequency and amplitude, and at least one applicator coil (32) for generating a low-frequency magnetic field corresponding to the electrical oscillations. Switching on of the apparatus and initiation of a treatment cycle is by actuating a single key switch (56, 58). The apparatus is normally switched off after expiry of a treatment period by a time switching device (80) but it can also be switched off by a fault detection circuit (88) which automatically switches the apparatus off on occurrence of disturbances. With this step operating errors and damage to the apparatus by disturbances are avoided even when the apparatus is used by laymen at home without supervision.

7 Claims, 2 Drawing Sheets

ELECTROMEDICAL APPARATUS FOR GENERATING LOW-FREQUENCY MAGNETIC FIELDS

FIELD OF THE INVENTION

The invention relates to an electromedical apparatus for generating low-frequency magnetic fields.

DESCRIPTION OF THE RELATED PRIOR ART

Apparatuses of the aforementioned type are known under the name MAGNETODYN apparatuses and are used to generate substantially sinusoidal magnetic fields having frequencies between about 2 and 30 Hz and field strengths up to about 5 mT such apparatuses are generically defined as electromagnetic apparatuses for generating low frequency magnetic fields consisting mainly of a generator section for generating a low frequency electric current of variable frequency and amplitude, and an applicator coil receiving said current to generate a corresponding low-frequency magnetic field. Either the magnetic fields themselves may be employed for the treatment, for example on loosening of joint endoprostheses, delayed healing of bone defects, disturbed wound healing, etc., or for induction of low-frequency alternating currents in implanted receiver coils for accelerating the healing of bone fractures, pseudoarthroses, etc., in accordance with the method of Kraus and Lechner.

To relieve medical surgeries and hospitals electromedical apparatuses of the type in question here are being increasingly hired out to patients for the duration of the treatment so that the treatment can be carried out at home. This results however in certain problems because the apparatuses must then normally be used by a layman without any assistance and supervision. The operation must therefore be very simple and unintentional or intentional manipulations and erroneous operations must be excluded. In addition, automatic securing against malfunctions is desirable because normally they cannot be recognized by the layman.

SUMMARY OF THE INVENTION

The present invention accordingly has as its object the provision of an electromedical apparatus for generating low-frequency magnetic fields which is simple, safe and reliable in operation so that it can be used without any problems by laymen as well.

The invention therefore proposes in an electromedical apparatus for generating low-frequency magnetic fields comprising a generator section which includes a means for generating low-frequency electrical oscillations, a means for setting the frequency of the oscillations, a means for setting the amplitude of the oscillations, a time control means for setting the duration of the oscillation generation, a mains unit for generating operating and bias voltages for said means and a mains switch for connecting the mains unit to a mains terminal, and at least one applicator coil which is connectable to the generator section and is fed by the low-frequency electrical oscillations for generating a low-frequency magnetic field corresponding to the electrical oscillations, the improvement in which the mains switch includes a key switch which is connected between the mains terminal and the mains unit and connects them as long as it is depressed, and a relay which comprises operating contacts connected in parallel with the key switch and a winding fed by the mains unit and the operating and bias voltages are supplied to said means directly without interposition of a further switching device so that the apparatus starts to operate when the mains switch is switched on.

BRIEF DESCRIPTION OF THE DRAWINGS

Hereinafter, a preferred example of embodiment of an electromedical apparatus according to the invention will be explained in detail with the aid of the drawings, wherein.

DESCRIPTION OF THE PREFERRED EMBODIMENT

Figure 1:
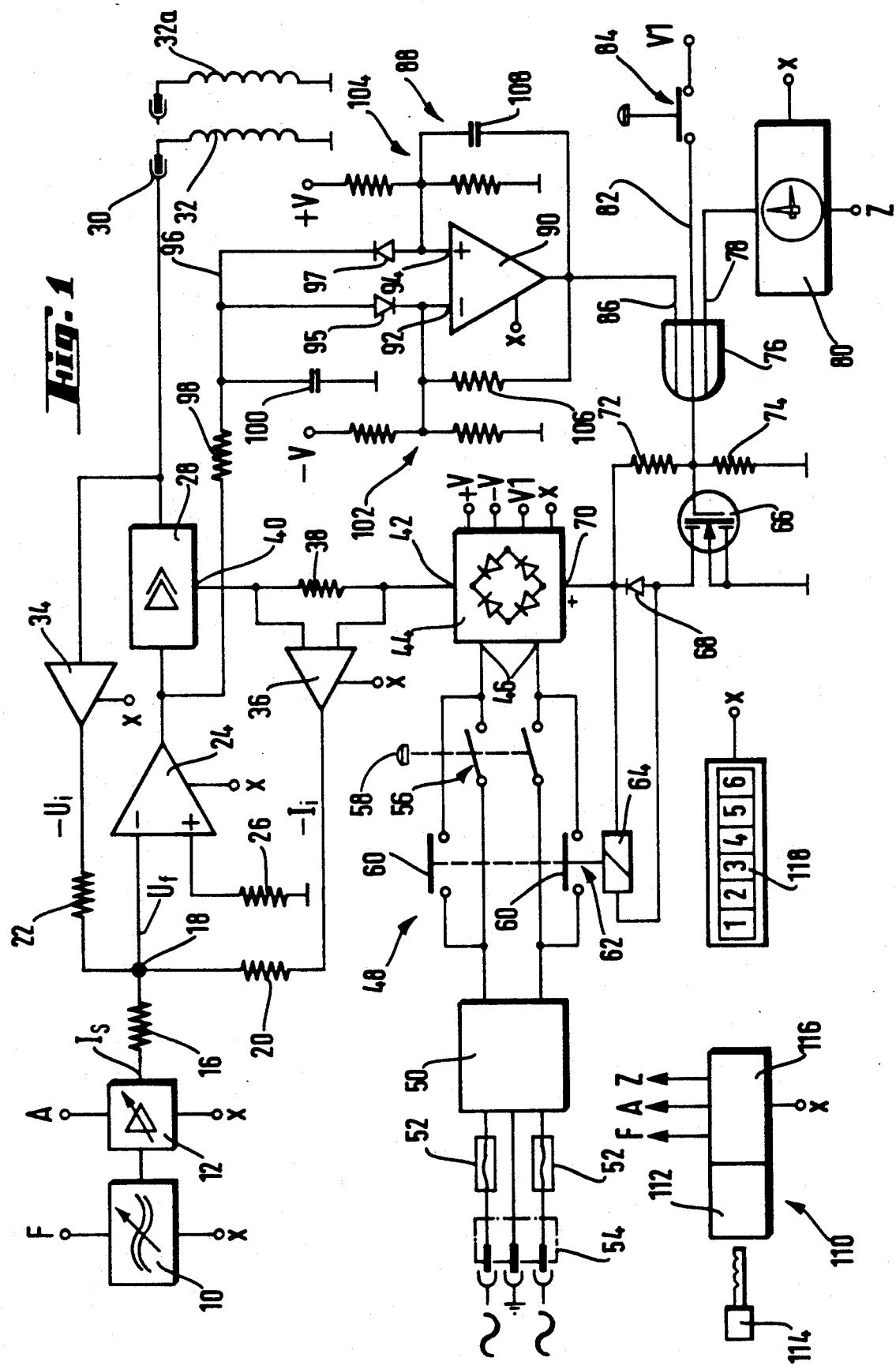
FIG. 1 shows a simplified circuit diagram of an apparatus according to an embodiment of the invention.

The apparatus illustrated in FIG. 1 includes a means for generating frequency-variable electrical oscillations in the form of a sine oscillator of which the frequency in the present example of embodiment is adjustable by a signal F to a desired value between 2 and 30 Hz. The sinusoidal oscillation from the output of the oscillator 10 is supplied to an amplifier circuit 12, the gain of which is adjustable by a signal A for setting the amplitude of the sine waves. The output signal of the amplifier circuit 12 represents a current desired value signal $I_s$ which is supplied via a resistor 16 to a summation point 18. Also supplied to the summation point 18 are a negative current actual value signal $-I_i$ via a resistor 20 and a negative voltage actual value signal $-U_i$ via a resistor 22. As a result, at the summation point 18 a control or error signal $U_f$ which is supplied to the negative input of a differential amplifier 24 of which the positive input is connected via a resistor 26 to ground. The output signal of the differential amplifier 24 is supplied to the input of a power and end amplifier circuit 28, the output of which is coupled to a terminal 30 for an applicator coil 32. A signal corresponding to the voltage at the applicator coil is also tapped from the output of the amplifier circuit 28 and supplied via an isolating amplifier 34 and the resistor 22 to the summation point 18 as voltage actual value signal.

The current actual value signal is generated by a differential amplifier 36, between the inputs of which a current tapping resistor 38 of small resistance value is connected and the output of which is coupled via the resistor 20 to the summation point 18. The current tapping resistor is connected between an operating voltage input 40 of the amplifier circuit 28 and a corresponding output 42 of a mains network 44 which includes a mains transformer and rectifier circuits and in the usual manner furnishes the operating voltages and biases necessary for the operation of the circuit arrangements of the apparatus.

The mains network 44 is coupled with its mains voltage input terminals 46 via a switching device 48, an interference suppression filter 50 and fuses 52 to a mains plug 54.

Figure 2:
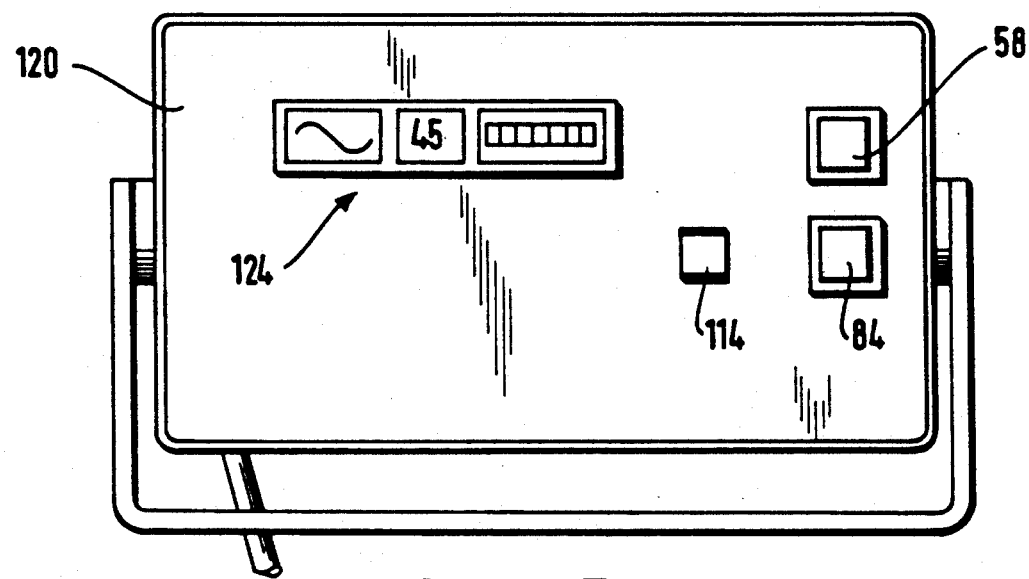
FIG. 2 is a front view of a practical embodiment of an apparatus according to FIG. 1

The switching device includes a two-pole key switch 56 which is biased by a spring, not illustrated, in the opening direction and connects the mains unit 44 to the mains for as long as a pushbutton 58 disposed at the front plate of the apparatus (FIG. 2) is depressed. Connecting in parallel to the contact sets of the key switch 56 are operating contacts 60 of an electromagnetic relay 62 having a winding 64.

The winding 64 is connected between an operating voltage terminal 70 of the mains unit 44 and the drain electrode of a field-effect transistor 66, the source electrode of which is connected to ground. The winding 64 is bridged with a protective diode 68. The gate of the field-effect transistor 66 receives a forward bias from the connecting point between two resistors 72 and 74 connected in series between the operating voltage terminal 70 and ground. The gate of the field-effect transistor 66 is also connected to the output of an OR member 76 which on excitation of at least one of its inputs furnishes an output voltage which renders the field-effect transistor 66 nonconductive, the relay winding 64 thereby becoming currentless. A first input 78 of the OR member is connected to a time control means 80, which when the apparatus is switched on by means of the switching device 48 receives from the mains unit 44 an operating voltage x, then starts to run and after a predetermined time (duration of a treatment cycle) defined by a signal Z furnishes an output signal to the input 78 of the OR member 76 which renders the field-effect transistor 66 nonconductive and thus causes the relay 72 to drop out so that the apparatus is switched off.

A second input 82 of the OR member is connected via a key switch 84, which enables the apparatus to be switched off immediately, to a bias terminal V1 of the mains unit 44. On depressing the key switch 84 the field-effect transistor 66 is likewise rendered nonconductive so that the relay 62 drops out.

A third input 86 of the OR member 76 is connected to a fault detection circuit 88 which on occurrence of a fault in the apparatus furnishes a disconnection signal to the OR member 76. The fault detection circuit 88 responds when in the normally sinusoidal output voltage of the differential amplifier 24 lying in the control loop asymmetries or excessively high signal amplitudes exceeding a predetermined threshold value in the positive or negative direction occur. The fault detection circuit 88 includes a differential amplifier 90, the output of which is connected to the input 86 of the OR member 76 and the inputs 92, 94 of which are each connected via a respective diode 95, 97, which are oppositely poled, to a line 96 which is connected via a resistor 98 to the output of the differential amplifier 24. Between the line 96 and ground a capacitor 100 is connected which prevents the fault detection circuit responding on occurrence of very brief interference signals. The inputs 92, 94 of the differential amplifier 90 are each connected to a bias circuit 102 and 104 respectively. The negative input 92 is also connected via a negative feedback resistor 106 to the output of the differential amplifier 90. A capacitor 108 is connected between the positive input 94 and the output. The fault detection circuit 88 does not supply an output signal for as long as the sinusoidal output voltage of the differential amplifier 24 is zero symmetrical and does not exceed corresponding threshold values either in the positive or in the negative direction. However, as soon as a fault occurs which results in an excessive wandering of the voltage at the output of the differential amplifier 24 the differential amplifier 90 generates an output signal which causes the relay 62 to drop out and thereby switches off the apparatus.

All the circuits and devices of the apparatus receive operating voltages x and biases only when the mains unit 44 is at the mains voltage. Thus, to initiate a treatment cycle it is only necessary to depress the pushbutton 58 and after expiry of the predefined treatment duration the apparatus is automatically switched off by the time control means 80. The previously frequently occurring error that either only the mains switch or only the start switch serving to initiate the treatment beginning was actuated and the apparatus was therefore not switched on cannot occur with the present apparatus.

A further securing against erroneous operating is achieved in that the treatment parameters, that is frequency, amplitude and duration of the treatment, cannot now be arbitrarily set by the patient but are governed by a coding unit 110. The coding unit includes a code switch 112 which is adjustable by insertion of a coding key 114 and furnishes address signals to a read-only memory (ROM) 116 which furnishes the signals F, A and Z, governing the frequency, the amplitude and the duration of a treatment cycle respectively, in accordance with the code of the coding key 114.

The control circuit having the components 16, 18, 20, 22, 24, 26 is designed for an 80% current control in combination with a 20% voltage control. This ensures a control-oscillation-free operation in the entire frequency range. The control ensures that the magnetic field strength defined by the amplitude signal A is largely independent of the frequency and independent of the type of applicator coil connected. The applicator coils 32, 32a, etc., are configured for this purpose as regards their cross-section and number of convolutions such that at a given current they all furnish the same magnetic field strength.

Figure 3:
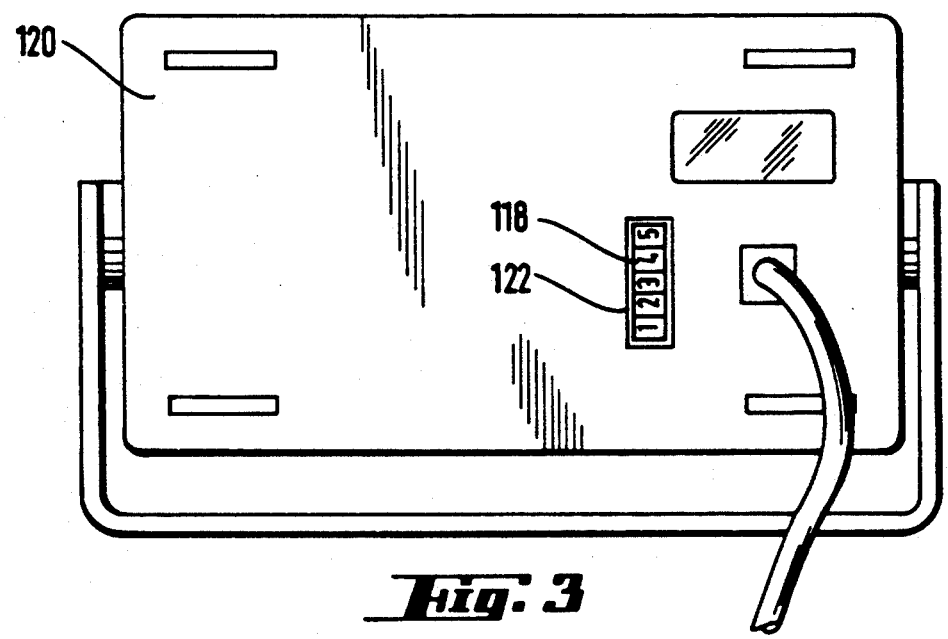
FIG. 3 is a view of the rear side of the apparatus according to FIG. 2.

To enable the total treatment duration to be determined an operating time counter 118 is provided which like all the other units receives an operating voltage x from the mains unit 44 for as long as the apparatus is switched on. The total operating time counter 118 is accommodated in the interior of the housing 120 (FIG. 3) of the apparatus and can be read through an inconspicuous slot 122 disposed at the rear side of the apparatus.

The front plate of the apparatus (FIG. 2) includes a display panel 124 for indicating the frequency, the duration of the instantaneous treatment cycle still remaining and the current and magnetic field amplitude. The circuits associated with the display panel are configured in usual manner and are therefore not illustrated.

I claim:

1. An electromedical apparatus for generating low-frequency magnetic fields comprising a generator section having a housing (120) and including
   a) first means (10) for generating low-frequency electrical oscillations,
   b) second means (110) for setting the frequency of the oscillations,
   c) third means (12) for setting the amplitude of the oscillations,
   d) fourth means for time control (80) for setting the duration of the oscillation generation,
   e) a mains unit (44) for generating operating and bias voltages for said first to fourth means and
   f) a mains switch (48) for connecting the mains unit (44) to a mains terminal (54), and
   g) sixth means (30) for coupling at least one applicator coil (32) to the generator section for receiving said low-frequency electrical oscillations to generate a low-frequency magnetic field corresponding to the electrical oscillations, wherein the mains switch (48) includes a key switch (56, 58) which is connected between the mains terminal (54) and the mains unit (44) and connects them as long as an activating key (58) is depressed, and a relay (62) which comprises operating contacts (60) connected in parallel with the key switch (56) and a winding fed by the mains unit (44), and the operating and bias voltages are supplied to said mains unit 44 directly without interposition of a further switching device so that the apparatus starts to operate when then mains switch is switched on.

2. An apparatus according to claim 1, wherein the electrical oscillations of adjustable frequency an amplitude are supplied as desired value signal ($I_s$) to a control circuit (16, 18, 20, 22, 24, 26) to which is also supplied a current actual value signal ($-I_i$) and a voltage actual value signal ($-U_i$) which are so dimensioned that the control operates primarily as current control and secondarily as voltage control.

3. An apparatus according to claim 2, wherein the control is an approximately 80% current control and approximately 20% voltage control.

4. An apparatus according to claim 1, comprising a fault detection circuit (88) to which a signal is supplied from a control loop and which on occurrence of an excess signal amplitude furnishes a disconnection signal which causes the relay (62) to drop out.

5. An apparatus according to claim 1, wherein a plurality of applicator coils (32, 32a) of different configurations is provided, said applicator coils of different configurations being so dimensioned as regards cross-section and number of turns that when fed with a predetermined current they all generate substantially the same magnetic field strength.

6. An apparatus according to claim 1, wherein a total operation time counter (118) is coupled to the mains unit (44), the total operating time counter (118) is arranged in the housing (120) of the apparatus and can be read through a slot (122) which is arranged at an inconspicuous point of the housing, for example the rear wall.

7. An apparatus according to claim 1, wherein operating parameters (F,A,Z) of the apparatus are selected by a coding unit (110) which in turn is set by a coding key (114) said operating parameters including frequency and amplitude of said oscillations and durations oscillation generation.

* * * * *